United States Patent [19]

Covington et al.

[11] 4,437,969
[45] Mar. 20, 1984

[54] OFFSET-GATE CHEMICAL-SENSITIVE FIELD-EFFECT TRANSISTORS (OG-CHEMFETS) WITH ELECTROLYTICALLY-PROGRAMMABLE SELECTIVITY

[75] Inventors: Arthur K. Covington, Newcastle upon Tyne; Alastair Sibbald, Whitley Bay, both of England

[73] Assignee: Corning Glass Works, Corning, N.Y.

[21] Appl. No.: 366,721

[22] Filed: Apr. 8, 1982

[30] Foreign Application Priority Data

Apr. 9, 1981 [GB] United Kingdom ............... 8111198

[51] Int. Cl.³ ..................... C12Q 1/00; G01N 27/46
[52] U.S. Cl. .................................. 204/403; 204/415; 204/416; 204/420; 357/25; 435/817
[58] Field of Search ......... 357/25; 204/195 R, 195 M, 204/195 B, 416, 420, 403, 415; 128/635; 324/71 SN, 71.5, 71.6; 435/817

[56] References Cited

U.S. PATENT DOCUMENTS

| 3,562,129 | 2/1971 | Simon . |
| 4,020,830 | 5/1977 | Johnson et al. ............ 204/195 B X |
| 4,180,771 | 12/1979 | Guckel .......................... 324/71 SN |
| 4,218,298 | 8/1980 | Shimada et al. ............... 128/635 X |
| 4,368,480 | 1/1983 | Senturia ............................... 357/25 |

FOREIGN PATENT DOCUMENTS

| 2736200 | 2/1979 | Fed. Rep. of Germany ........ 357/25 |
| 1505343 | 3/1978 | United Kingdom ................ 204/412 |

OTHER PUBLICATIONS

Martin A. Afromowitz et al., J. Bioengineering, vol. 1, pp. 55–60, (1977).
Helen James et al., Anal. Chem., vol. 44, No. 4, pp. 856–857, (1972).
M. Neshkova et al., J. Electroanal. Chem., 102, pp. 189–198, (1979).
Piet Bergveld, IEEE Trans. on Biomedical Engineering, vol. BME-19, No. 5, pp. 342–350, (1972).
Ching-Chang Wen et al., IEEE Trans. on Electron Devices, vol. ED-26, No. 12, pp. 1945–1951, (1979).

*Primary Examiner*—G. L. Kaplan
*Attorney, Agent, or Firm*—W. S. Zebrowski

[57] ABSTRACT

A selective chemosensitive microelectronic transducer is provided for the detection and measurement of chemical properties, by engineering a field-effect transistor such that source 6 and drain 7 regions are connected to bonding pads 2 and 4, and the semiconductor bulk connected to pad 1. The metal gate 8 is extended laterally to a remote area 9, and also to bonding pad 3 via a narrow metallization track 5 designed to support only a limited, predetermined electrical current in the manner of a fusible link. External electrical access to the device is achieved with wirebonding 14, and the device is selectively sealed with an inert, impervious encapsulation material 10 such that only gate area 9 remains exposed. Electroactive materials are deposited over the offset-gate area 9, or electrodeposited using connection through 8, 5 and 3. Subsequently, link 5 is open-circuited by pulsed electrical overload, creating a floating chemosensitive gate.

8 Claims, 3 Drawing Figures

OFFSET-GATE CHEMICAL-SENSITIVE FIELD-EFFECT TRANSISTORS (OG-CHEMFETS) WITH ELECTROLYTICALLY-PROGRAMMABLE SELECTIVITY

FIELD OF THE INVENTION

The present invention relates to a novel chemosensitive microelectronic transducer for use in the detection and measurement of various chemical properties. "Chemical properties", as used herein, shall be understood to include ion activity and concentration, presence and concentration of enzymes, substrates, antibodies, antigens, hormones and reducible gases, and the presence, concentration and activity of any of a variety of chemical and biochemical substances including the constituents of enzymatic systems, e.g. serum enzymes, glucose, lactates, pyruvates, creatinine, urea and the constituents of the immunochemical system.

DESCRIPTION OF THE PRIOR ART

Selective electrodes for the measurement of ionic activity (ion-selective electrodes or I.S.E.s) are well known. [See A. K. Covington (ED.), Ion-selective electrode methodology (Vols. I and II) CRC Press, Florida, 1979.] They are used extensively in analytical chemistry, for process monitoring and for clinical application. Such electrodes are costly and difficult to fabricate, are inherently fragile, and possess high electrical impedance which requires that electrical connections be carefully screened and that high-impedance buffer amplifiers be used to process the signal. The object of the present invention is to provide a novel chemical sensitive microelectronic device offering distinct advantages over the prior art and readily capable of integration into more sophisticated and elaborate microelectronic transducer elements.

In previous attempts to simplify the manufacture of I.S.E.s, there are many reports in the scientific literature of 'coated-wire' electrodes (for example, James H., Carmack, G. and Freiser, H., Anal. Chem. (1972), 44 (4) 856-7), where an electroactive material, such as an ion-selective glass, doped polymer or other substance, is coated directly on to an inert metallic wire; platinum is commonly used for this purpose. Various types of ion-selective electrodes have been made in this way, but the metallic/polymer interface is irreversible, or polarizable, and does not support D.C. electrical conduction. When coupled to the relatively high electrical load that the electrode is required to drive, the resulting electrical performance is poor. Alternatively, other electroactive agents may be applied to a bare-wire electrode by electroplating, as described in the report of Neshkova and Sheytranov (J. Electroanal. Chem (1979) 102, 189-98) where the authors used the electrodeposition of copper selenide on to a platium base to form electrodes specifically responsive to copper.

An improvement on conventional coated-wire electrode technology has been suggested by Afromovitz, M. A. and Yee, S. S. (J. Bioeng. (1977) 1, 55-60) where an electroactive material is deposited on to a thin metallic film using well-known thick-film screening processes, and located directly adjacent to a metal-oxide-semiconductor field-effect transistor (MOSFET) mounted conveniently on the same substrate, thus forming a hybrid chemical transducer of robust nature, small dimensions and fabricated using a mass-production compatible process. Such sensors are, however, not well suited to the simultaneous measurement of more than one parameter.

Thin ion-selective films deposited on silicon substrates have been proposed in a previous U.K. patent (Butler, J. F., 1978, 1505343) for use as passive ion-selective electrodes with the suggestion that such films would be compatible with on-chip amplification, but there is no disclosure as to how this may be achieved.

Since 1970 there have been reported several types of chemical sensitive microelectronic device, principally the ion-sensitive field-effect transistor (ISFET) (Bergveld, P. (1972) IEEE Trans. Biomed. Eng., BME 19, 342–51) and the ion-controlled diode ICD) (Wen, C. C., Chen, T. C. and Zemel, J. N. (1979) IEEE Trans. Electron Devices ED-26, (12) 1945–51) based respectively on their conventional well-known counterparts, the MOSFET and the gate-controlled diode (GCD). ISFETs offer unique advantages over conventional measuring electrodes in analytical chemistry, in terms of size, robustness, utility, cost and mass-production potential. Their construction is similar to that of the well-known MOSFET transistor, but having an electroactive membrane substituted for the gate metal such that it lies directly over, and in intimate contact with, the gate insulation material. However, there are several severe problems which are presently inhibiting the industrial development of ISFET devices, concerning adequacy and methodology of encapsulation, and long-term electrical stability. It is an object of the present invention to obviate such problems by use of a structurally different sensor having major advantages over conventional I.S.E.s and prior art in the field of ISFETs and other microelectronic chemical transducers.

SUMMARY OF THE INVENTION

According to the present invention, there is provided a semiconductor device for the detection and measurement of chemical properties, hereinafter referred to as an offset-gate chemical-sensitive field-effect transistor (OG-CHEMFET), which may be optionally provided with electrolytically-programmed selectivity (EPS) if so required.

Thus, the invention provides a selective, chemical-sensitive field-effect device comprising a MOSFET-type transistor having the gate conductor (8) directly or indirectly laterally extended (9) and covered to part by an electroactive material or materials suitable for the detection and measurement of chemical properties in which the device is exposed.

The structure of the OG-CHEMFET can be physically implemented or engineered in a number of ways, and the following description is intended to illustrate the principles and mode of operation of the device and ot to define rigidly the structure and/or dimensions.

DETAILED DESCRIPTION OF THE INVENTION

Figure 1A:
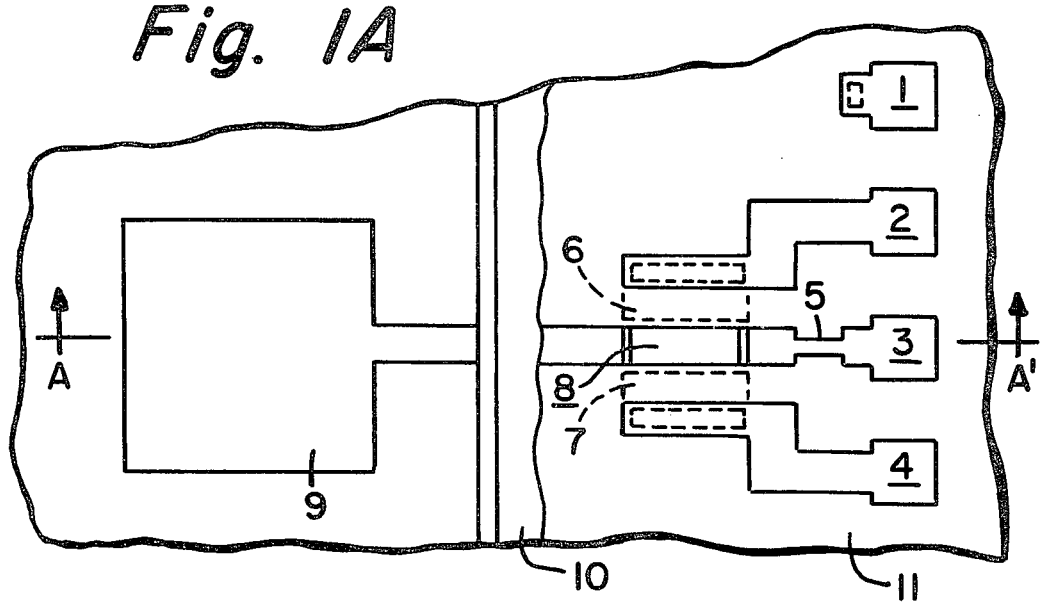
FIG. 1 shows an OG-CHEMFET structure in plan (FIG. 1A) and front elevation through plane A—A' (FIG. 1B)
Figure 1B:
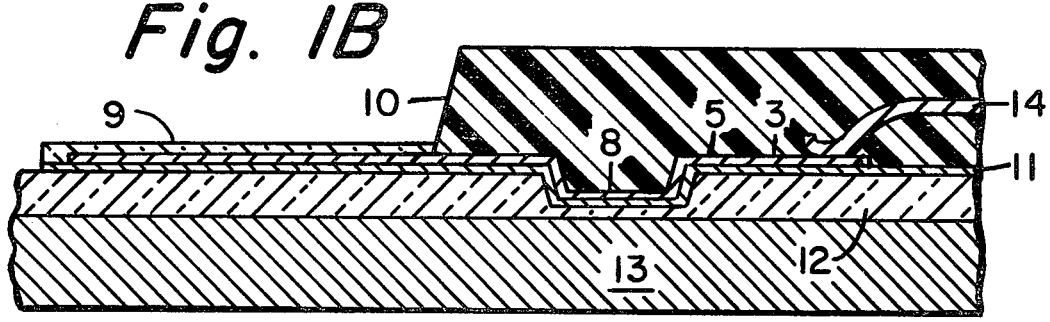

As shown in FIG. 1 and described in more detail below, a selective chemosensitive microelectronic transducer is provided for the detection and measurement of chemical properties, by engineering a field-effect transistor such that source 6 and drain 7 regions are connected to bonding pads 2 and 4, and the semiconductor bulk connected to pad 1. The metal gate 8 is extended laterally to a remote area 9, and also to bonding pad 3 via a narrow metallization track 5 designed to support only a limited, predetermined electrical current in the manner of a fusible link. External electrical access to the device is achieved with wire-bonding 14, and the device is selectively sealed with an inert, impervious encapsulation material 10 such that only gate area 9 remains exposed. Electroactive materials are deposited over the offset-gate area 9, or electrodeposited using connection through 8, 5 and 3. Subsequently, link 5 is open-circuited by pulsed electrical overload, creating a floating chemosensitve gate.

The basis of the OG-CHEMFET is a MOSFET-type element which will be familiar to those skilled in the art and comprises two adjacent diffused semiconductor regions 6 and 7 of a certain polarity fabricated in a semiconductor substrate of opposite polarity, such that they are separated by a short channel, over which is deposited or grown an insulating film 12 (preferably $SiO_2$), an ion-barrier film 11 (preferably $Si_3N_4$) and a thin metal gate film 8. We do not exclude the use of a lightly doped channel, or metallurgical channel, between regions 6 and 7 such that a depletion-mode device is formed. [See Allison, J., Electronic Integrated Circuits, McGraw-Hill, London, 1975.] The type of gate metal may be chosen from a variety of suitable elements or alloys, including platinum, aluminium, chromium, gold or composites thereof. Alternatively, a doped polysilicon gate can be employed for increased chemical durability. The $SiO_2$ insulating film 12 is thinner (50 nm) over the gate region than the rest of the device (500 nm). Metallic, ohmic connection is made to the semiconductor bulk 13 and to the diffused regions via suitably etched holes in the insulators by the deposition of thin metallic films in such a way that external electrical access can be made to suitable bonding pads 2 and 4 using wire-bonds 14 formed by techniques commonly used in the microelectronics industry. A bonding pad 3 is also provided for external connection to the metal gate 8 of the device, but this connection can be made through a fusible link 5 if so required. That is to say, section 5 between the device gate 8 and the bonding pad 3 is substantially narrower than the rest of the metallization and, being thus engineered to support a predetermined limited current only, can be deliberately destructively open-circuited by the application of a current overload between pad 3 and electrolytic connection to the electroactive area 9, thus permanently isolating the device gate. If electrolytic programming is not required, link 5 and pad 3 may be omitted.

The metal gate 8 of the field-effect transistor 6,8,7, which may be chromium, gold, aluminium or other suitable metal, is extended laterally to form an offset-suitable gate area 9 as shown in FIG. 1, on to which suitable electroactive materials may be deposited or plated prior to or after encapsulation in a suitably inert encapsulating agent 10 or material. Epoxy cements or silicon rubbers are the most commonly used agents for this purpose in other chemosensitive microelectronic devices such as ISFETs, but we propose an improved material and encapsulation process in part of our copending U.S. patent application Ser. No. 366,722 entitled "Encapsulted Chemoresponsive Microelectronic Device Arrays and a Method for the Fabrication of the Same" filed on even date herewith. The encapsulation material is applied selectively so as to expose the chemosensitive area of the device to the solution whilst enclosing the electrically active section. A portion of encapsulating material 10 is illustrated as being broken away to reveal the various device components that are disposed on the surface of film 11. The rest of the device is also required to be electrically insulated from exposure to electrolyte in a similar manner to ISFET devices. This can be achieved by engineering the OG-CHEMFET device or array of devices, so that the bonding pads are orientated outwards on the silicon substrate, and the electroactive areas disposed centrally, such that the outer perimeter of the silicon can be encapsulated leaving the central area exposed.

Ion-selective membranes are deposited over, or plated on to, the offset-gate 9. In this context conventional, well-known electroplating techniques are possible by virtue of electrical connection to this area via the gate metal 8, fusible link 5 and bonding pad 3, after which link 5 may be deliberately destroyed by a pulsed electrical overload as described hereinbefore to leave the offset-gate structure 9 and 8 electrically isolated, thus forming a 'floating' gate.

Many ion-selective films may be deposited in this manner. Electroplated metallic silver forms an "electrode of the first kind" selective to silver ions in solution, and which, if required, may be electrolytically chloridised to form a silver/silver chloride electrode useful as an $Cl^-$ and/or $Ag^+$ responsive electrode. This in turn may be coated with a potassium chloride-filled gel to form a reference electrode.

Chalcogenide films described supra for the detection of copper ions can be plated on to the offset-gate, and replaced when required by etch removal and subsequent replating. Alternatively, if aluminium is used as the gate metal, area 9 may be anodically oxidised to form a thin $Al_2O_3$ film which is known to be pH responsive. Some other metal oxides such as that of rhodium are relatively inert and suitable for use as a pseudo-reference electrode.

Ion-responsive materials may be applied by other techniques. Ion-selective glasses may be deposited by RF-sputtering, chemical vapour deposition (CVD) or electron-beam evaporation. Polymeric materials doped with electroactive substances may also be applied by techniques already known and used in I.S.E. prior art. For example, the macrocyclic antibiotic valinomycin used as the dopant in a PVC matrix (Simon, W., U.S. Pat. No. 3,562,129) forms a highly selective potassium-responsive membrane. Plastic materials which are polymerized in an electric field may be used as the carrier matrix.

Chemically inert materials may be deposited on the offset-gate 9 for the purposes of forming a chemically unresponsive surface such that the electrical properties of the OG-CHEMFET can be controlled by the bulk electrical potential of the electrolyte to which it is exposed, allowing a closed-loop pseudo-reference system to control the electrolyte potential, and obviating the requirement for a conventional reference electrode with the system. In this context, CVD formation and esterification of the material known by the registered trade-mark Parylene has been useful in ISFET prior art, or RF-sputtered polytetrafluoroethylene (PTFE) may be employed.

The novel OG-CHEMFET structure provides the following advantages over other types of chemosensitive microelectronic devices, including the ISFET:

1. The gate area exposed to solution is remote from the active channel of the device which reduces ionic contamination of the channel dielectric, a well known source of electrical drift and device failure, and facilitates the encapsulation process.
2. There is no lateral electric field induced in the electroactive membrane by the highfield area in the device channel, as exists in the ISFET and which is considered to be detrimental to rapid, stable response.
3. The active channel is covered by gate metal which acts as an optical mask and virtually eliminates optical sensitivity to which ISFET devices are prone.
4. The electrical connections between the active channel and the appropriate bonding pads are largely metallic, as opposed to highly doped semiconductor material used in ISFET devices. This substantially reduces the overall temperature sensitivity and also improves the electrochemical efficiency of the devices. In addition, integration of the chemosensitive device with other microelectronic circuitry is more readily achieved.
5. Electrolytic-programming of device selectivity can be achieved, allowing various different types of structure to be formed on the same semi-conductor element. This feature is attractive for commercial exploitation as many different multiple-sensor transducers can be created using a single semi-conductor element as a foundation.
6. The OG-CHEMFET is tested and characterized more easily during development and production because electrical access to the gate is available. If the fusible-link is allowed to remain intact, calibration and recalibration procedures are simplified during on-line monitoring, but at the penalty of degraded noise immunity.
7. The OG-CHEMFET structure is more readily integrated into other associated on-chip circuitry, such as multiplexers, than the ISFET. For example, an array of OG-CHEMFETs is suitable as current injection sources for feeding the input of a charge-coupled device, arranged so as to form a parallel-to-serial multiplexer in a manner analogous to present state-of-the-art charge-coupled-device image sensors.

Figure 2:
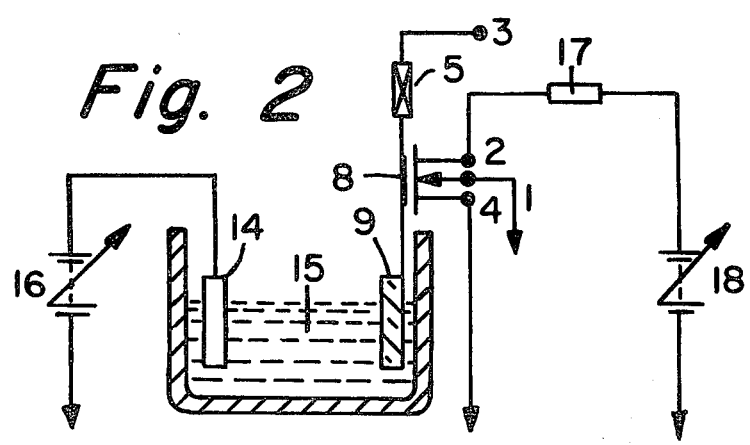
FIG. 2 shows one possible mode of operation of the device. We do not exclude the use of other circuit configurations or other forms of electronic interfacing to the device, either remotely or locally situated, or fully integrated with the semiconductor structure to form a transducer or transducer array of enhanced capability.

The functional operation of the OG-CHEMFET is shown in FIG. 2. The FET part of the structure is connected in source-follower mode and will be familiar to those skilled in the art. Source 4 and bulk 1 connections are grounded and the drain connection 2 is connected through a resistor 17 to an external voltage source 18. Electrical connection 3 is initially present to the gate 8 via a fusible link 5. The offset-gate area 9 is coated with electroactive material and exposed to the electrolyte sample 15 which is to be analysed, housed in a plastic container. The electrolyte is electrically referred to ground via a conventional reference electrode 14 and a voltage source 16 in order to bias the device into a favourable region of operation. Voltage source 16 may not be necessary if depletion-mode devices are employed.

The potential of the offset-gate is set with respect to ground by ion-exchange reactions between the electroactive substance deposted on to gate and the electrolyte under analysis, as in conventional ion-selective electrode methodology. This potential controls the surface charge density of the channel in the FET structure, and hence the drain current flowing between the source and drain regions due to the external voltage source 18. Changes in drain current are reflected by changes in the potential of the drain connection 2.

There are various ways in which the OG-CHEMFET can be physically engineered: we do not exclude any such ways from the scope of the present invention. For example, a diffused channel could be used to link the offset-gate 9 and the active gate 8, or a doped polysilicon film incorporated instead of metallization, possibly beneath the ion-barrier film, to minimise lateral electrolyte penetration of the encapsulant/device interface.

The electrolytic programming technique described herein is also appropriate for application to other chemosensitive semiconductor devices, such as ion-controlled diode arrays.

We claim:

1. A field-effect device comprising a semiconductor substrate, a source region located in a first surface of said substrate, a drain region located in said first surface and spaced apart from said source region, a layer of electrical insulator material overlying at least a portion of said source and drain regions and the surface of the substrate lying between said regions, a gate conductor disposed over said insulator material between said source and drain regions, a planar, offset gate comprising a conductive layer disposed on said first surface in a region remote from said source and drain regions, conductive means for electrically connecting said conductive layer to said gate conductor, an electrical conductor connected to said conductive layer, and a fusible link connected in series with said electrical conductor.

2. A field-effect device according to claim 1 wherein said conductive means comprises a layer of conductive material disposed on the surface of said substrate.

3. A field-effect device according to claim 2 wherein said conductive means and said conductive layer are extensions of said gate conductor.

4. A field-effect device according to claim 1 further comprising a layer of electroactive material suitable for the detection and measurement of chemical properties disposed over at least a portion of the surface of said conductive layer.

5. A field-effect device according to claim 1 wherein said conductive means and said conductive layer are extensions of said gate conductor, said device further comprising a layer of electroactive material suitable for the detection and measurement of chemical properties disposed over at least a portion of the surface of said conductive layer.

6. A field-effect device according to claim 5 further comprising a coating of inert encapsulating material extending over that portion of said substrate including said source and drain regions to an area of said substrate between said source and drain regions and said conductive layer, whereby said electroactive material is exposed.

7. A field-effect device comprising a semiconductor substrate, a source region located in a first surface of said substrate, a drain region located in said first surface and spaced apart from said source region, an electrical insulator material overlying at least a portion of said source and drain regions and the surface of the substrate lying between said regions, a gate conductor disposed over said insulator material between source and drain regions, said gate conductor extending laterally along said first surface to a region remote from said source and drain regions, the width of that portion of said gate conductor in said remote region being greater than the width of said gate conductor in the region of said source and drain regions, at least a portion of said lateral extension of said gate conductor being covered by at least one electroactive material suitable for the detection and measurement of chemical properties to which the device is exposed, an electrical conductor connected to said conductive layer, and a fusible link connected in series with said electrical conductor.

8. A field-effect device according to claim 7 further comprising a coating of inert encapsulating material extending over that portion of said substrate including said source and drain regions to an area of said substrate between said electroactive material and said source and drain regions whereby said electroactive material is exposed.

* * * * *